United States Patent [19]

Benson et al.

[11] Patent Number: 4,736,156

[45] Date of Patent: Apr. 5, 1988

[54] APPARATUS FOR ON-LINE DETERMINATION OF DIELECTRIC CONSTANT

[75] Inventors: Warren E. Benson, Needham; Stanley Breen, Norwood, both of Mass.

[73] Assignee: Forte Technology, Inc., Norwood, Mass.

[21] Appl. No.: 850,942

[22] Filed: Apr. 11, 1986

[51] Int. Cl.$^4$ .................. G01N 27/02; G01R 27/26
[52] U.S. Cl. ................ 324/61 R; 324/61 P; 324/61 QS
[58] Field of Search ............ 324/61 P, 61 R, 61 QS, 324/65 P

[56] References Cited

U.S. PATENT DOCUMENTS

| | | | |
|---|---|---|---|
| 3,025,465 | 10/1959 | Breen | 324/61 R |
| 3,488,758 | 1/1970 | Benson et al. | 324/61 R |
| 4,555,661 | 11/1985 | Benson et al. | 324/61 R |

Primary Examiner—A. D. Pellinen
Assistant Examiner—Leon K. Fuller
Attorney, Agent, or Firm—Davis, Hoxie, Faithfull & Hapgood

[57] ABSTRACT

An improved apparatus for the "on-line" measurement of the dielectric constant or percent moisture of a material such as tobacco moving within the walls of a pipe or chute is disclosed. A differential capacitive technique is used for the measurement. The apparatus consists of a four electrode device, with two of the electrodes attached to the outside of the walls of the pipe or chute, and two of the electrodes attached to the inside of the walls of the pipe or chute. The two inner electrodes are connected by switches to the two outer electrodes, respectively, so that first and second capacitances appear at the output terminals of the electrode device depending upon the position of the switches. The output terminals of the electrode device are connected to an oscillator which produces an output signal indicative of the frequency of the oscillator's oscillation which is proportional to the capacitance at the terminals of the electrode device. The output signal of the oscillator is connected to a microprocessor which is used to calculate a value proportional to the change in capacitance of the electrode device when the switches are closed. This value can be used to determine the dielectric constant or the percent moisture of the material in the chute.

6 Claims, 2 Drawing Sheets

APPARATUS FOR ON-LINE DETERMINATION OF DIELECTRIC CONSTANT

FIELD OF THE INVENTION

This invention relates to an improved apparatus for the "on-line" measurement of the dielectric constant of a material confined within the walls of a pipe, chute or the like.

BACKGROUND OF THE INVENTION

The dielectric constant of a material is a fundamental physical property of the material and is important in research and development and for the control of industrial processes. For example, careful control of the amount of moisture (which is related to dielectric constant) in a stream of tobacco moving through a pipe or chute is important because if the percent moisture in the tobacco is not within specified restricted ranges, the tobacco will not "cure" properly. Since the dielectric constants of water and tobacco are quite different (water 80, tobacco 5) a technique to rapidly, conveniently and accurately measure the dielectric constant of a stream of tobacco in a chute or pipe is very useful.

Also, shipping costs of a material, where based on gross weight, may be needlessly increased by extra moisture in the material.

One way of determining dielectric constant involves capacitance measuring, as the capacitance of a capacitor is proportional to a constant determined by the physical dimensions of the electrodes of the capacitor and the distance between the electrodes multiplied by the dielectric constant of the material between the electrodes. For example the capacitance, C, in farads, of a parallel plate capacitor is approximated by the well known equation $$C = K(eA)/d \qquad \text{Equation (1)}$$

where K is a constant, e is the dielectric constant of the material between the plates of the capacitor, A is the area of the plates and d is the distance between the plates. In addition to the area of the electrodes and the distance between them, the "end effects" of the electrodes affect the capacitance.

One technique for determining dielectric constant by capacitance methods is shown in U.S. Pat. No. 3,025,465, assigned to the assignee of the present application. In that patent, a sample of material is placed in a test cell which consists of two plates separated by a certain fixed distance. A first set of capacitance measurements is taken, first with the test cell empty and then with the material in the cell. Then, the spacing between the plates is changed by physically moving one of the plates. A second set of capacitance measurements is taken, first with the cell empty and then with the material in the cell. The dielectric constant of the material is determined from the ratio of the difference between the capacitances measured with the material in the test cell and the difference between the capacitances measured with the test cell empty, that is, filled only with air which has a known dielectric constant.

The difference between the capacitances measured with the test cell empty can also be used to calibrate a measuring instrument. Then, the dielectric constant of an unknown material can be determined using the difference between the capacitances measured with the unknown material in the test cell in conjunction with the calibrated measuring instrument. Further details of such measuring techniques are found in U.S. Pat. No. 3,025,465.

U.S. Pat. No. 3,488,758, assigned to the assignee of the present application, also utilizes a capacitance measuring method for determining dielectric constant. However, in that patent, capacitance is not measured directly. Rather, the plates of the test cell are connected across the terminals of a free-running oscillator. The capacitance across the plates of the cell serves as the capacitance of the oscillator. The frequency of the oscillator is gated to a counter so as to produce an increasing count for a predetermined time interval during which the plates are separated by a first distance. As in U.S. Pat. No. 3,025,465, the distance between the plates of the test cell is then changed by moving one of the plates after the first measurement. This count process is repeated and the residual count remaining on the counter is a count proportional to the change in capacitance as a result of movement of the plates. As described above, the dielectric constant of the material can then be determined using a second set of differential measurements for a material having a known dielectric constant, for example, air.

Both of the above patents have the disadvantage that they require that a plate be moved in carrying out the measurement process. Movement of a plate adds time, complexity and cost to the measurement process and also increases the probability of measurement error because position measurement of the movable plate is not perfectly repeatable.

U.S. Pat. No. 4,555,661, also assigned to the assignee of the present application, utilizes a capacitance measuring method for determining the dielectric constant of liquids, slurries, gases, or solids which can be made to flow, without the necessity of physically moving a plate during the measurement process. As in U.S. Pat. No. 3,488,758, the '661 patent does not measure capacitance directly.

The '661 patent discloses in one embodiment a three electrode device which is placed in a vial containing a material for which the dielectric constant is to be determined. Two of the electrodes are connected across the terminals of a free-running oscillator. The third electrode is located between the first and second electrodes. A switch is connected between the first and third electrodes so that the third electrode is at a floating electrical potential when the switch is open. Closing the switch electrically switches the third electrode from a floating electrical potential to an electrical potential equal to that of the first electrode. The first and second electrodes are connected to a free-running oscillator which is in turn connected to a bi-directional counter. With the switch open, the capacitance for the free-running oscillator is primarily determined by the area of the first and second electrodes, the separation of the electrodes and the dielectric constant of the material between those electrodes. A first count, in an increasing direction, of the frequency of the oscillator is made by the bi-directional counter over a predetermined time period. The switch is then closed, thereby electrically switching the third electrode to the electrical potential of the first electrode, and thus changing the value of the capacitance of the free-running oscillator because the distance between the two "plates" of the capacitor has effectively been decreased. A second count, in a decreasing direction, of the frequency of the oscillator is made by the bi-directional counter, leaving a residual count in the bi-directional counter. The dielectric constant of a first material is determined by obtaining a residual count using the above procedure for a second material having a known dielectric constant. A residual count for the first material is then obtained. Since the ratio of the unknown dielectric constant of the first material is proportional to the ratio of the residual counts for the two materials, the dielectric constant of the unknown material can be readily determined from the measured residual counts.

A further embodiment of the '661 patent utilizes a microprocessor to replace the bi-directional counter and perform the counting function, control the switch and determine the dielectric constant by interpolating from a stored table of residual counts for materials of known dielectric constants.

A further embodiment of the '661 patent utilizes five electrodes in a so-called split stator arrangement, which creates a balanced electric field, and two switches. This five electrode embodiment functions in a similar fashion to the three electrode embodiment to determine dielectric constant.

Often, it is desired to measure the dielectric constant of a material "on-line", i.e., without having to remove a sample of the material from a continuous processing of the material. The apparatus described in U.S. Pat. No. 4,555,661 cannot always be used to determine "on-line" the dielectric constant of a material where the material is moving through the inside of a pipe, chute or the like as part of a process. For example, if the electrode device of the '661 patent is used for an "on-line" measurement of the dielectric constant of a stream of tobacco slowly moving through a pipe or chute, the electrodes, which would have to be placed directly into the tobacco, would significantly interfere with the movement of the stream of tobacco and would most likely cause the stream to stop moving, or "bridge" creating air pockets, thus unacceptably interfering with the process.

Further, the electrode device of the '661 patent cannot accurately measure the dielectric constant of the tobacco, or any other bulk solid or powder which does not flow like a liquid, because the electrodes of the device, when stuck into the tobacco, break up the solid structure of the tobacco, creating unacceptably large air pockets. The dielectric constant measured by the '661 patent apparatus would not accurately reflect the dielectric constant of the tobacco only because a significant part of the measurement would represent the dielectric constant of the air pockets. Because the tobacco, when broken up by the electrodes, would not evenly "flow" around the electrodes, the dielectric constant measurement made by the '661 patent apparatus would not accurately reflect the dielectric constant of the tobacco.

Other examples of bulk solids or powders which do not flow like a liquid, for which the '661 apparatus would not be adequate, are coffee beans, nuts, powdered detergents and certain pharmaceuticals.

SUMMARY OF THE INVENTION

This invention relates to an improved method and apparatus for the "on-line" measurement of the dielectric constant of a material confined within the walls of a pipe, chute or the like. According to the present invention, a differential capacitance technique is used. It is a feature of this invention that both the area and the end effects of the electrodes are held essentially constant for the entire measurement procedure.

The apparatus consists of a four electrode device which is attached to the walls of a pipe, chute or the like through which the material is moving. The material is confined within inside portions of first and second walls of the chute or pipe.

The first electrode is attached, preferably by an adhesive, to the outside portion of the first wall. Similarly, the second electrode is attached to the inside portion of the first wall.

The third and fourth electrodes are likewise attached to the inside and outside portions of the second wall, respectively.

The first and fourth electrodes are connected across the terminals of a free-running oscillator. A first switch is connected between the first and second electrodes so that the second electrode is at a floating potential when the first switch is open. Closing the switch electrically switches the second electrode from a floating potential to an electrical potential equal to that of the of the first electrode. A second switch is connected between the third and fourth electrodes so that the third electrode is at a floating potential when the second switch is open. Closing the switch electrically switches the third electrode from a floating potential to an electrical potential equal to that of the of the fourth electrode.

The first and fourth electrodes are connected to a free-running oscillator which is in turn connected to a counter. With the first and second switches open, the capacitance for the free-running oscillator is primarily determined by the area of the first and fourth electrodes, the separation of the electrodes and the dielectric constants of the material between the first and second walls and of the walls themselves. A first count of the frequency of the oscillator is provided by the counter which in one embodiment is a bi-directional counter. This first count from the bi-directional counter is an increasing count made during a predetermined time, for example, one tenth of a second.

The switches are then closed, thereby electrically switching the second electrode to the electrical potential of the first electrode and the third electrode to the electrical potential of the fourth electrode. A second count of the frequency of the oscillator is made by the counter. For the bi-directional counter, this count is in a decreasing direction for the same predetermined time period as used for the first count, leaving a residual count in the bi-directional counter.

The dielectric constant of a first material is determined by obtaining a residual count using the above procedure for a second material having a known dielectric constant. Then, a residual count for the first material is obtained. Since the ratio of the unknown dielectric constant of the first material to the known dielectric constant of the second material is proportional to the ratio of the residual counts for the two materials, the dielectric constant of the unknown material can be readily determined from the measured residual counts.

In a further embodiment, a microprocessor is employed. The microprocessor replaces the counter and performs the counting function, controls the switches, and determines the dielectric constant, for example, by interpolating from a stored table of residual counts for materials of known dielectric constants.

DETAILED DESCRIPTION OF THE INVENTION

Figure 1:
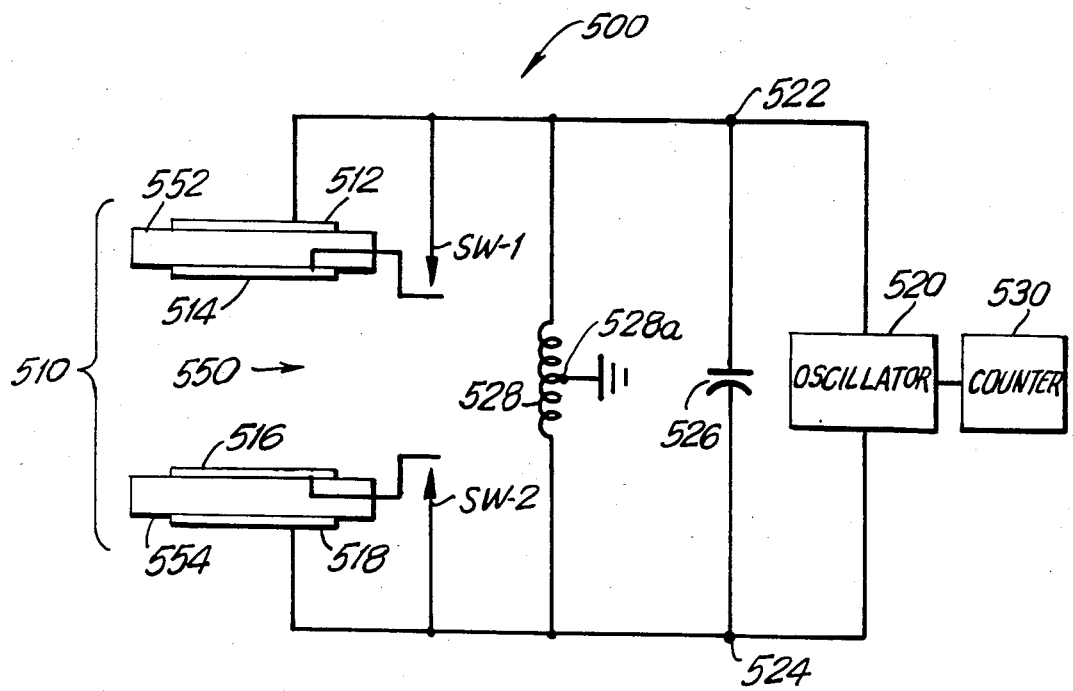
FIG. 1 is a block diagram of an embodiment of the present invention including an electrode device attached to the walls of a chute wherein material is confined within the chute by the walls of the chute.

FIG. 1 shows a block diagram of a system 500 according to an embodiment for determining the dielectric constant of a moving stream of material, for example a bulk solid or powder such as tobacco, moving through the inside of a pipe or chute 550, in accordance with the present invention.

The material in the chute 550 is confined by a first wall 552 and a second wall 554 of the chute 550, and moves between the inside portion of the first wall 552 and the inside portion of the second wall 554. In the present embodiment, the walls 552 and 554 are made of an acrylic plastic, though any non-conductive medium may be used in the present invention for the walls 552 and 554.

System 500 includes an electrode device 510 having electrodes 512, 514, 516 and 518. Electrode 512 is attached to the outside portion of wall 552. The attachment means is preferably an adhesive or plastic screws. However, any number of attachment means suggest themselves to one skilled in the art.

Similarly, electrode 518 is attached to the outside portion of wall 554. Electrodes 514 and 516 are likewise attached to the inside portions of walls 552 and 554, respectively.

Electrode 512 is connected to a switch SW-1 and to a first terminal 522 of a free-running oscillator 520. Electrode 518 is connected to a switch SW-2 and to a second terminal 524 of the free-running oscillator 520. A capacitor 526 and an inductor 528 are connected across the terminals 522 and 524 of the oscillator 520. Inductor 528 has a center tap 528a which is grounded. The grounding of the center tap 528a of the inductor 528 insures that there is a balanced electrical field across the electrode device 510, thus minimizing the effect on the measurement of dielectric constant of an uneven distribution of the material in the chute 550.

Electrode 514 is connected through switch SW-1 to the electrode 512 so that when switch SW-1 is open electrode 514 is at a floating potential and when switch SW-1 is closed electrode 514 is connected to electrode 512 and terminal 522. Similarly, electrode 516 is connected through switch SW-2 to the electrode 518 so that when switch SW-2 is open electrode 516 is a floating electrical potential and when switch SW-2 is closed electrode 516 is connected to electrode 518 and terminal 524.

The oscillator 520 produces a buffered output signal indicative of the frequency of oscillation of oscillator 520. The form of this buffered output signal is such that the pulsations of the output signal can be counted by a counter. This output signal is connected to an input of a counter 530, which in one embodiment is a bi-directional counter.

System 500 functions to determine the dielectric constant of the material in the chute 550 as follows. The electrode device 510 is attached to the walls 552 and 554 as previously described. Initially, the electrodes 512 and 518 are connected across the terminals 522 and 524 of the free-running oscillator 520. Switches SW-1 and SW-2 are open, and thus electrodes 514 and 516 are initially at a free-floating electrical potential. The area of the electrodes 512 and 518, the distance between electrodes 512 and 518 and the dielectric constants of the material in the chute 550 and the walls 552 and 554 determine the capacitance as measured across the electrodes 512 and 518. The frequency of the oscillator 520 will vary in proportion to the capacitance contributed by the electrode device 510.

With the stream of tobacco moving through the chute 550 and switches SW-1 and SW-2 open, the bi-directional counter 530 counts the number of pulses in the output signal of oscillator 520 occurring in a predetermined time, for example, one-tenth of a second. The counter 530 makes this first count in an increasing direction. In other words, during the first count, counter 530 counts "up".

A second count is then made with switches SW-1 and SW-2 closed. As a result, electrodes 514 and 516 are at an electrical potential equal to that of electrodes 512 and 518, respectively, during the second count. When the switches SW-1 and SW-2 are closed, the capacitance seen at the terminals of the electrode device 510 changes. This capacitance change results in a change in the frequency of oscillator 520. The bi-directional counter 530 counts a second count in a decreasing direction for the same time period as used for the first count. In other words, counter 530 counts "down".

Following the second count, a residual count is left in the counter 530. Since both the first and second counts are for the same duration of time, this residual count represents the change in the fundamental frequency of the oscillator 520 from the first to the second measurement. This change in frequency is a result of the change in capacitance seen at the terminals of the electrode device 510 between the first and second measurements. Consequently, the residual value of the counter 530 can be used to determine the dielectric constant of the material in the chute 550 in an analogous manner to that which is explained in U.S. Pat. Nos. 3,025,465, 3,488,758 and 4,555,661, which are herein incorporated by reference.

By way of example, the dielectric constant of the material in the chute 550 can be determined from the residual count by conducting similar differential measurements using materials in the chute 550 with known dielectric constants, for example, air which has a dielectric constant of 1. In U.S. Pat. No. 3,025,465, the dielectric constant of an unknown material is found in the ratio of the difference in capacitance measured with the unknown test material to the difference in capacitance measured with a known material. Alternatively, the dielectric constant of the unknown material can be determined using a calibration chart produced using representative residual counts for materials of known dielectric constants.

In a preferred embodiment, the counter 530 is part of a microprocessor. The microprocessor is also used to provide control signals to operate switches SW-1 and SW-2 for the predetermined time period and count the pulses from oscillator 520. The microprocessor directs that switches SW-1 and SW-2 be opened for the first count and closed for the second count for the predetermined time period. The microprocessor subtracts the second count from the first count to obtain the frequency difference count. The dielectric constant of the material in the chute 550 is calculated directly by the microprocessor, for example, by interpolation from a conversion table prepared using known materials. This conversion table is stored in the memory of the microprocessor.

In a further preferred embodiment, the switches SW-1 and SW-2 are commercially available reed relays. A reed relay provides fast, positive switching and has only a small stray capacitance. The usual configuration of a reed relay consists of a metal reed with a movable contact at one end and a fixed contact at the other end. The relay is mounted and sealed in a small glass tube. The relay is made of ferromagnetic material so that it may be activated (deflected) by a solenoid mounted externally to the glass reed. A small current through the solenoid may be generated by a manual switch or by some external electrical switching command, such as a command from a microprocessor.

In addition to being used to determine the dielectric constant of a material in the chute 550, the apparatus 500 may also be used to determine the percent moisture of a material in the chute 550, for instance tobacco. Empirical results show that the percent moisture of the material in the chute 550 can be determined using the following equation:

$$\%M = (A)\log_{10}((F-J)/W) + B + R(T-20) \quad \text{Equation (2)}$$

where
- $\%M$ = the percent moisture content of the material;
- $W$ = the density of the material;
- $T$ = the temperature of the material;
- $F$ = the residual count remaining in the counter 530 after the first and second counts are taken with material such as tobacco in the chute 550, as described above;
- $A$, $B$ and $R$ are constants empirically determined for the specific material in the chute 550; and
- $J$ = a constant representing the residual count in the counter 530 when the first and second count are taken in the manner detailed above, with no material in the chute 550 (i.e., with air in the chute 550).

Figure 2:
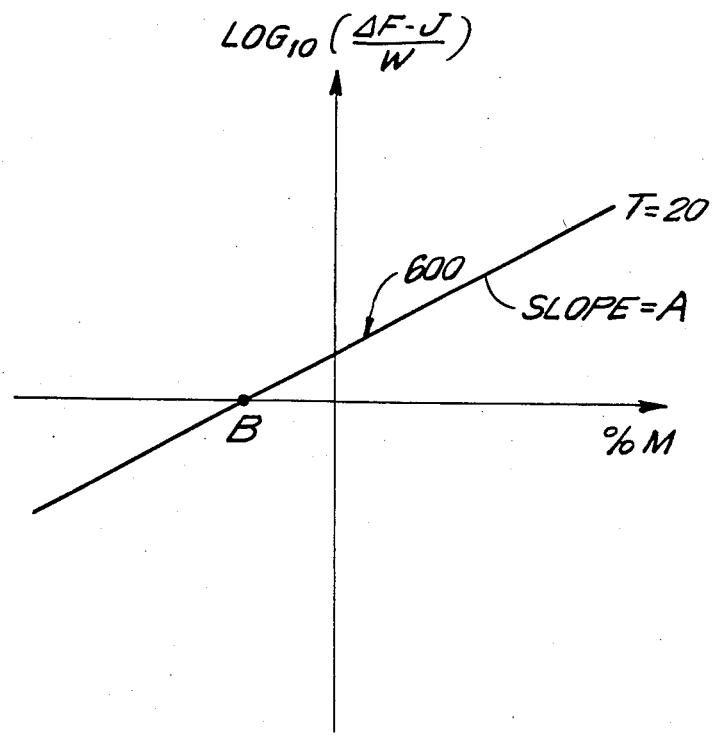
FIG. 2 is a graph related to an equation for determining the percent moisture of a material using the apparatus of the present invention.

The values of the constants A and B can be graphically determined in the following manner. Using two or more samples of material at 20 degrees centigrade ($T=20$), with each sample at a different known moisture content, the data is plotted with the term $\log_{10}((F-J)/W)$ on the "Y" axis and the percent moisture on the "X" axis, as shown generally in FIG. 2. Plotting the data will result in an approximate straight line 600, also as shown generally in FIG. 2. The value for the constant A can be determined from the graph by calculating the slope of the line 600. The value of the constant B is the intercept of the line 600 with the "X" axis of the graph of FIG. 2.

The value of "J" in equation (2) should be determined occasionally to correct for (a) the long-term aging and dimensional changes in the electrode device 510; (b) the long-term aging and dimensional changes in the walls 552 and 554; and (3) the long-term changes in the dielectric constant of the walls 552 and 554.

Once A and B are known, R, which represents the empirically derived temperature coefficient for equation (2), can be determined by solving equation (2), above, using a sample of the material of a known percent moisture, but at a temperature other than $T=20$, for instance, $T=30$ degrees centigrade.

Also, as previously described, the system 500 self-compensates for drift of the oscillator 520 as the electrodes 512, 514, 516 and 518, being of the same size and shape and having similar end effects, produce a change in capacitance primarily due to the change in dielectric constant of the material flowing in the chute.

Once A, B and R have been empirically determined, the percent moisture of any sample can be calculated using equation (2). The microprocessor can easily be programmed to provide a direct read out of percent moisture based on equation (2).

It is readily seen that the apparatus of the present invention permits the measurement "on line" of the dielectric constant and the moisture content of a material without interfering with the movement of the material in a process, since the electrodes of the apparatus are attached directly to the walls of the pipe or chute which confine the movement of the material. Further, the electrode device of the present invention can be easily attached to whatever confinement means, for instance the walls of a pipe or chute, are used to confine the material. This allows greater flexibility in adapting the apparatus of the present invention to any number of different processes.

Also, as previously described, the apparatus of the present invention permits the "on-line" measurement of the dielectric constant of a bulk solid or powder which cannot be made to "flow" like a liquid.

We claim:

1. Apparatus for measuring the dielectric constant of a material confined within inside portions of first and second walls of a chute or pipe comprising;
   an electrode device with first, second, third and fourth electrodes with the first electrode attached to the outside portion of the first wall, the second electrode attached to the inside portion of the first wall, the third electrode attached to the inside portion of the second wall and the fourth electrode attached to the outside portion of the second wall;
   first and second terminals at first and second electrical potentials, respectively;
   means for connecting the first electrode to the first terminal and the fourth electrode to the second terminal;
   means for placing the second and third electrodes at a floating electrical potential;
   means for switching electrically the second electrode from the floating electrical potential to the first electrical potential;
   means for switching electrically the third electrode from the floating electrical potential to the second electrical potential;
   measuring across the first and fourth electrodes a first value of an electrical signal proportional to the capacitance across the first and fourth electrodes, while maintaining the area and the end effects of the electrodes essentially constant;
   electrically switching the second electrode from the floating electrical potential to an electrical potential equal to the first electrical potential;
   electrically switching the third electrode from the floating electrical potential to an electrical potential equal to the second electrical potential; and
   measuring across the second and third electrodes a second value of an electrical signal proportional to the capacitance across the second and third electrodes, while maintaining the area and the end effects of the electrodes essentially constant, whereby said first and second values are used to calculate the dielectric constant or the percept moisture of a material.

2. Apparatus as in claim 1 wherein the first and second electrodes are attached to the first wall and the third and fourth electrodes are attached to the second wall by means of an adhesive.

3. Apparatus as in claim 1 wherein the first and second electrodes are attached to the first wall and the third and fourth electrodes are attached to the second wall by means of plastic screws.

4. Apparatus as in claim 1 wherein the means for switching comprises a first reed relay located between the first and second electrodes and a second reed relay located between the third and fourth electrodes.

5. Apparatus as in claim 1 including a free-running oscillator connected across the first and second terminals wherein the first value is a first frequency of the oscillator with the first and fourth electrodes connected to the first and second terminals, respectively, and the the second value is a second frequency of the oscillator with the second and third electrodes connected to the first and second terminals, respectively.

6. Apparatus as in claim 5 wherein a bi-directional counter is gated to the oscillator and the counter counts in an increasing direction pulses at the first frequency for a predetermined time, counts in a decreasing direction pulses at the second frequency for a time period equal to the predetermined time.

* * * * *